US006430442B1

(12) United States Patent
Peters et al.

(10) Patent No.: US 6,430,442 B1
(45) Date of Patent: Aug. 6, 2002

(54) SPLIT CONTACT WITH SUPER ELASTIC RETAINING RING FOR IMPLANTABLE MEDICAL DEVICE

(75) Inventors: Charles E. Peters; James J. Christenson, both of NE. Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/515,262

(22) Filed: Feb. 29, 2000

(51) Int. Cl.[7] ............................................. A61N 1/375
(52) U.S. Cl. ........................................ 607/37; 607/38
(58) Field of Search ............................... 607/9, 37, 38; 128/897

(56) References Cited

U.S. PATENT DOCUMENTS

| | | | |
|---|---|---|---|
| 5,458,629 A | 10/1995 | Baudino et al. ............ 607/116 |
| 5,730,628 A * | 3/1998 | Hawkins ...................... 607/37 |
| 5,849,032 A | 12/1998 | Van Venrooij .............. 607/123 |
| 6,198,969 B1 * | 3/2001 | Kuzma ......................... 607/37 |

* cited by examiner

Primary Examiner—Carl Layno
(74) Attorney, Agent, or Firm—Banner & Witcoff, Ltd.

(57) ABSTRACT

A construction and method are employed for connecting leads and extensions that minimizes the need for set screws, and the times and physical efforts required of surgeons for connecting leads and connector blocks is reduced. An improved electrical and mechanical connector for the conductor comprises at least two components. First a multi-piece body forms a receptor for the conductor. At least one of the body pieces is electrically conductive. Second, an elastic member retains together the body pieces of the multi-piece body. The elastic member biases the body pieces into mechanical, restraining contact with the conductor, and biases the electrically conductive body piece into electrical contact with the conductor, when the conductor is introduced into the receptor. The elastic member further elastically yields under mechanical force to permit introduction of the conductor into the receptor.

22 Claims, 3 Drawing Sheets

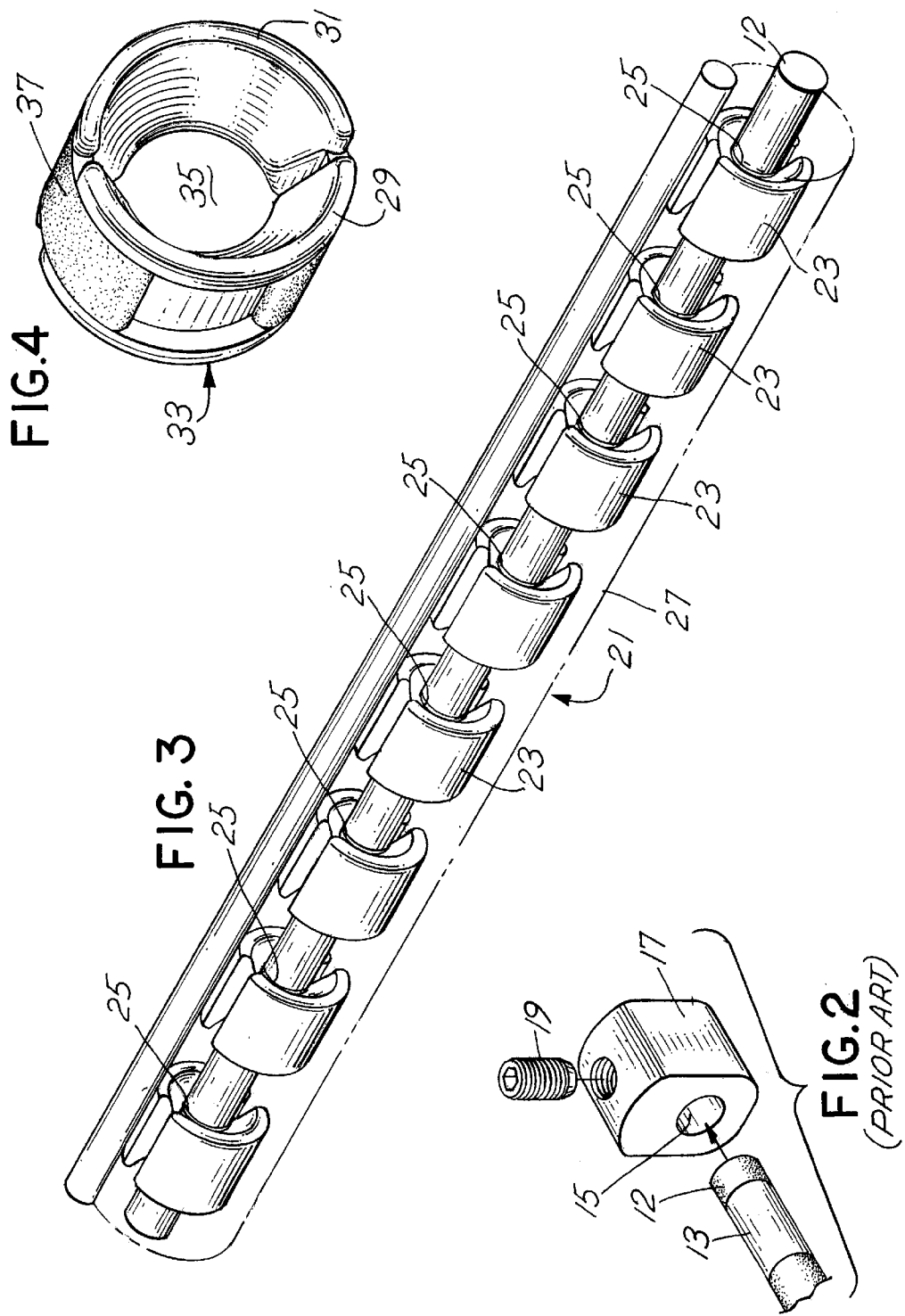

SPLIT CONTACT WITH SUPER ELASTIC RETAINING RING FOR IMPLANTABLE MEDICAL DEVICE

BACKGROUND OF THE INVENTION

This invention relates to implantable medical devices for the human body, for electrical stimulation to the spinal cord and peripheral nervous system. More specifically, the invention relates to the mechanical and electrical connection of leads, extension cables, and implantable pulse generators in such implantable medical devices.

Briefly, APT Neurostimulation ("Advanced Pain Therapy Neurostimulation") is available from Medtronic, Inc., and commonly used for neuropathic pain. APT Neurostimulation, used for both spinal cord stimulation and peripheral nerve stimulation, uses a small neurostimulation system that is surgically placed under the skin to send mild electrical impulses to the spinal cord or nerves. The electrical impulses are delivered through a lead that is also surgically placed, near the spinal cord or the nerve selected to be stimulated. These electrical impulses block signals of pain from reaching the brain. Medtronic APT Neurostimulation systems include the Itrel® 3 system, consisting of an implantable pulse generator (IPG), a patient programmer, an extension, a lead(s), and a connector block. This system is totally implantable—no part is outside the body. The IPG generates precise, electrical pulses to control pain. The IPG contains a special battery and electronics to create these pulses. The unit, which is about 2.25 inches (6 cm) across, less than one-half inch (1 cm) thick and about 2 inches (5.2 cm) high, is most often placed under the skin of the abdomen. The lead is a small medical wire with special insulation. It commonly has four or eight electrodes, small, exposed electrical contacts, through which electrical stimulation is delivered. It also commonly has a corresponding four or eight internal wires for separate electrical connection to each electrode, for selective use of the electrodes in providing stimulation. The lead is placed such that the electrodes are next to the spinal cord or peripheral nerve to be stimulated. The extension is a small cable about 20 inches (50 cm) long that is placed under the skin and connects the lead to the IPG.

In addition to treating pain, Medtronic devices assist patients with other concerns. The Medtronic InterStim® Therapy for Urinary Control offers an approach for managing urinary urge incontinence, nonobstructive urinary retention, and significant symptoms of urgency-frequency in patients who have failed or could not tolerate more conservative treatments. The implantable InterStim Therapy system uses mild electrical stimulation of the sacral nerves, in the lower region of the spine, that influence the behavior of the bladder, sphincter, and pelvic floor muscles. As with APT Neurostimulation, a lead is surgically implanted, an extension runs to a neurostimulator, and the neurostimulator acts as an IPG to send precise, electrical pulses to your sacral nerves to control the treated symptoms.

In variations of these devices, alternate systems include devices that are implanted, along with devices that are external such as accessories for increased battery life.

To date, the electrical and mechanical connections of the lead to the extension in neurological implants are accomplished by a connector block including a series of set screw blocks. Leads are inserted in metal set screw blocks, and metal set screws press against proximal ring contacts on the leads and press the contacts against the blocks, to clamp them in place and cause electrical connection between the lead wires and the blocks. U.S. Pat. No. 5,458,629 issued Oct. 17, 1995, to Baudino, for an Implantable Lead Ring Electrode and Method of Making, briefly describes the connector blocks and associated lead structure, at column 4, lines 5–16, and that description is incorporated by reference.

SUMMARY OF THE INVENTION

A primary object of the invention is to substantially advance the construction and method employed for connecting leads, extensions and IPGs in the connector blocks of neurological implants.

Another primary object is to minimize the need for set screws in connector blocks for placing leads in the human body for spinal cord and peripheral nerve stimulation. Most preferably, the connection of leads, extensions, and IPGs becomes "tool-less."

Other primary objects include substantially reducing the times and physical efforts required of surgeons for connecting leads and connector blocks, and reducing the lengths of implantation surgeries, while maintaining the substantial benefits that flow from excellent electrical and mechanical connection of leads, extensions and IPGs.

In a principal aspect, the invention is incorporated in body implantable apparatus for implantation in a living human body, for delivering electrical stimulation to at least one nerve of the body, where the apparatus includes an implantable pulse generator (IPG), for generating the electrical stimulation, and an implantable wire-like electrical lead for delivering the stimulation from the IPG to the desired site of stimulation. The lead is of the type having a distal portion for placement at the site and a proximal portion, the proximal portion including multiple proximal electrical contacts on its surface. In this environment, the invention is an improved connector block for electrical and mechanical connection of the proximal portion of the lead into the apparatus, for example, by connection to an extension. The improved connector block comprises a plurality of multi-piece bodies each forming a receptor opening for a proximal electrical contact, at least one of the body pieces of each body being electrically conductive adjacent the receptor opening. A plurality of elastic members each retain together the body pieces of one of the multi-piece bodies, bias the body pieces into mechanical, fixating contact with a proximal electrical contact, and bias the electrically conductive body piece into electrical contact with the proximal electrical contact, when the proximal electrical contact is introduced into the receptor opening. The elastic member is, further, elastically yieldable under mechanical force to permit introduction of the proximal electrical contact into the receptor opening.

In another principal aspect, and more generally, the invention includes an improvement in body implantable apparatus for implantation in a living body, for delivering electrical stimulation to the nervous system of the body, the apparatus including a wire-like electrical conductor. In this aspect, the invention takes the form of an improved electrical and mechanical connector for the conductor. This connector comprises at least two components. First, a multi-piece body forms a receptor for the conductor. At least one of the body pieces is electrically conductive. Second, an elastic member retains together the body pieces of the multi-piece body. The elastic member biases the body pieces into mechanical, restraining contact with the conductor, and biases the electrically conductive body piece into electrical contact with the conductor, when the conductor is introduced into the receptor. The elastic member further elastically yields under mechanical force to permit introduction of the conductor into the receptor. The conductor may be a lead, an extension, or other perhaps similar electrical conductor.

As preferred, the multi-piece body includes multiple duplicate pieces arranged circumferentially around the receptor, most preferably two such pieces, both electrically conductive. In this construction, the elastic member circumferentially retains together the body pieces. The multi-piece body forming the receptor for the conductor consists of two arcuate, duplicate pieces arranged circumferentially around the receptor. Also as most preferred, the arcuate pieces of the multi-piece body have conical insertion guiding surfaces, sloped inwardly toward the center of the pieces, on both sides of the center. Further as most preferred, the elastic member includes a superelastic material, such as nickel titanium alloy, and the member is C-shaped and positioned in a groove around the body pieces. The conductor and receptor may have an interference fit, if desired.

Substantial further understanding is provided by the Detailed Description of the Preferred Embodiment, which follows a brief description of the drawing.

BRIEF DESCRIPTION OF THE DRAWING

A drawing accompanies this specification, and includes a variety of figures. They are each briefly described as follows:

FIG. 2 is a sketch of a prior art set screw block for connecting a lead to an extension in a prior art nerve stimulation unit.

FIG. 3 is a perspective view of a connector block according to the preferred embodiment of the invention.

FIG. 4 is a perspective view of a single multi-piece body and elastic member of the preferred connector block.

Reference numbers are used consistently throughout the figures.

DETAILED DESCRIPTION OF THE PREFERRED EMBODIMENT

Figure 1:
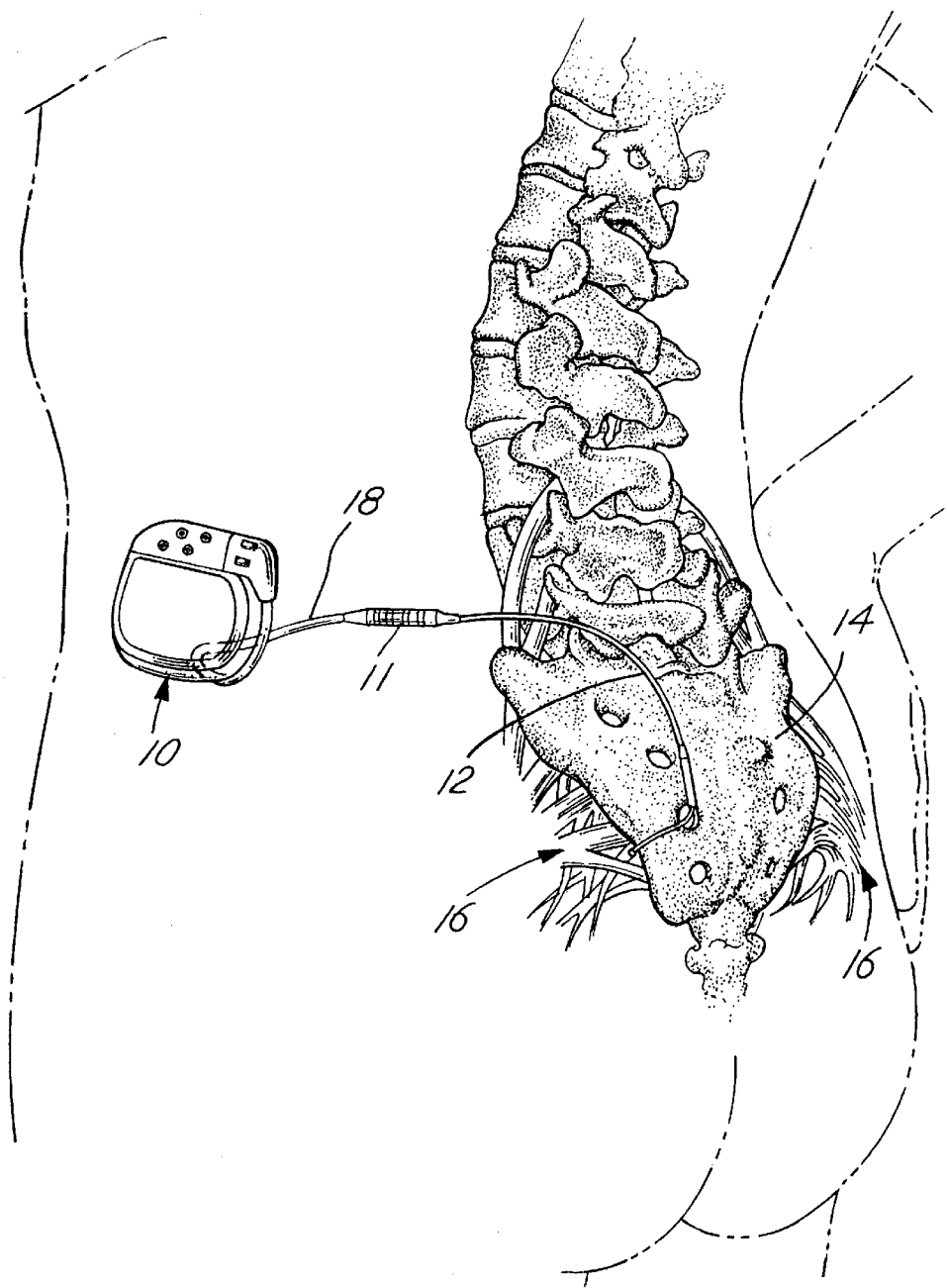
FIG. 1 is a diagrammatic view of a human patient in which a preferred form of nerve stimulation unit has been implanted for sacral nerve stimulation.
Figure 5:
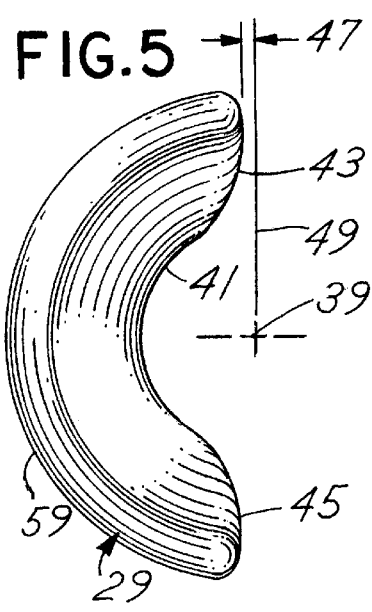
FIG. 5 is a side view of a piece of the multi-piece body of FIG. 4.
Figure 6:
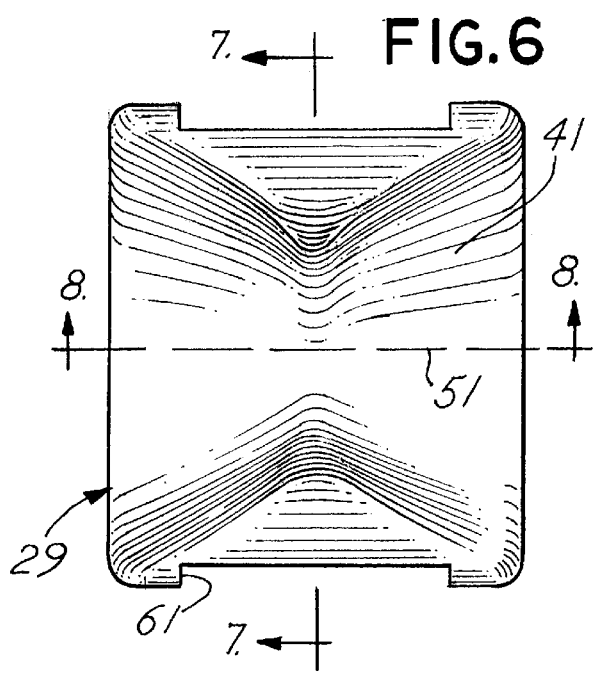
FIG. 6 is a view of the piece of FIG. 5, taken from the right in FIG. 5.

As referenced above, the currently available Medtronic InterStim® Therapy for Urinary Control offers an approach for managing urinary urge incontinence, nonobstructive urinary retention, and significant symptoms of urgency-frequency in patients who have failed or could not tolerate more conservative treatments. The implantable InterStim Therapy system uses mild electrical stimulation of the sacral nerves that influence the behavior of the bladder, sphincter, and pelvic floor muscles. Referring to FIG. 1, as with APT Neurostimulation, an IPG 10 contains a special battery and electronics to create electrical stimulation pulses. The IPG 10 is most often placed under the skin of the abdomen, as shown. The lead 12 is a small medical wire with special insulation. and contains a set of electrodes (small electrical contacts) through which electrical stimulation is delivered. This stimulation is often described as tingling. The extension 18 is a small cable about twenty inches (fifty cm) long that is placed under the skin and connects the lead 12 to the IPG 10. The connector block 11 connects the lead 12 and extension 18. For Medtronic InterStim® Therapy for Urinary Control, the lead 12 is anchored to the sacrum 14 near the sacral nerves 16.

Referring to FIG. 2, and as stated in U.S. Pat. No. 5,458,629, at column 4, lines 5–16, both in the prior art and in connection with the invention, the lead 12 terminates in a series of proximal electrical, ring contacts 13 (one shown). In the prior art connector block, during surgery, the lead 12 is threaded through an axially aligned series of openings 15 (one shown) in set screw blocks 17 (one shown). With the lead so threaded, and again during surgery, a series of set screws 19 (one shown) are screwed into the blocks 17, to drive the contacts 13 against the blocks 17 and fix them in place. This construction is highly desirable in the security of its connection of the contacts 13 and blocks 17. Electrical connection is secure because mechanical connection is secure. Nevertheless, this construction requires the use of tools during surgery, to drive the set screws 19 into place.

Referring to FIG. 3, the now-preferred connector block 21 includes a series of "split ring" contacts 23, one for each proximal ring electrode 25 on the lead 12. Electrical wires (not shown) are welded to the exterior of the contacts 23, and the series of contacts 23 are overmolded in silicon rubber 27 or harder material to form the block 21.

Referring to FIG. 4, each split ring contact 23 includes two or more pieces in the form of split ring members 29, 31 of a multi-piece body in the form of a split ring 33. The pieces and body form a receptor in the form of a central opening 35 for the lead 12. As preferred, the split ring members 29, 31 are stainless steel, and thereby electrically conductive. When wires are welded or otherwise electrically connected to the contacts 23, they are welded or connected to the split ring members 29, 31.

An elastic member in the form of a split ring retainer 37 retains the members 29, 31 in the form of the split ring 33 as shown. As in FIG. 3, the retainer 37 biases the members 29, 31 into mechanical, restraining, and electrical contact with the lead 12, when the lead 12 is in the opening 35. The retainer 37 is elastic to yield under mechanical force to permit the lead 12 to enter the opening 35.

Figure 7:
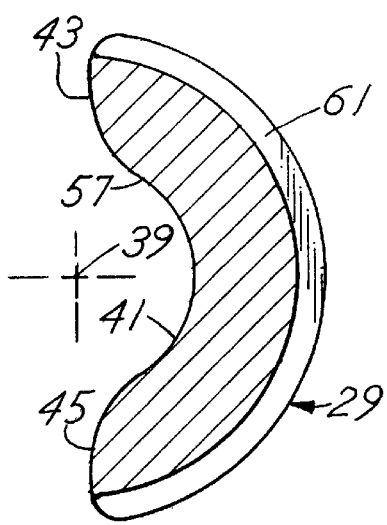
FIG. 7 is a cross-section view taken along line 7—7 in FIG. 6.
Figure 8:
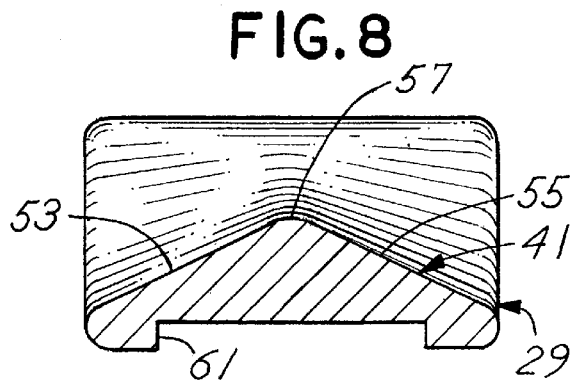
FIG. 8 is a cross-section view taken along line 8—8 in FIG. 6.

Referring to FIGS. 5–8, the most preferred members 29, 31 are duplicates of each other, such that one representative member 29 is shown. The member 29 extends radially about a remote center 39, as seen in side view, in FIG. 5. An inner wall 41 is arcuate, spanning about 172 degrees of extent around the center 39. The wall 41 tapers outward to opposed end walls 43, 45, each offset a short distance 47 from a line 49 defining 180 degrees of extent around the center 39. Axially along an axis 51 through the center 39 (see FIG. 6 for axis 51), and as best seen in FIG. 8, the inner wall 41 includes two inwardly, centrally sloping lands 53, 55 terminating in a central, inward-most apex 57. The axial extent of the lands 53, 55 along axis 51 exceeds substantially the inward extent of the lands 53, 55. The apex 57 defines the innermost extent of the member 29, at diameter A from center 39, as seen in FIG. 7.

Figure 9:
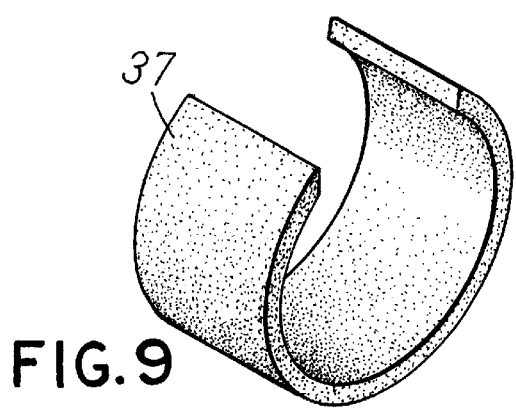
FIG. 9 is a perspective view of the elastic member of the connector block of FIG. 3.

An outer wall 59 is also arcuate, with the same extent about the center 39 as the inner wall 41. The outer wall 59 also tapers into the end walls 43, 45, inwardly. An outer groove 61 is elongated in the direction of the axis 51, and comparatively shallow in the radial direction toward the center 39. Referring to FIG. 9, the retainer 37 is laterally elongated and radially thin. The groove 61 fits the retainer 37, as seen by comparing FIGS. 8 and 9, and as shown in FIG. 4.

The retainer 37 circumscribes, or extends around, about 283 degrees around the split ring contact 29, and is thus C-shaped. The retainer 37 is preferably a superelastic material, most preferably nickel titanium (NiTi) alloy. This alloy is commercially available as Nitinol from Memory Corporation.

The split ring contact 23 is interference fit to the lead 12. When parts such as ring members 29, 31 and retainer 37 are assembled, with the ring in the groove 61 of the ring members 29, 31, the opening 35 for the lead 12 defined by the apexes 57 of the members 29, 31 has a diameter smaller than the outer diameter of the proximal electrical contacts of the lead 12. Mechanical force of the lead 12 on the either land 53 or 51 of the members 29, 31 drives the members 29, 31 apart, against the resistance of the retainer 37, enlarging the opening 35. When a contact 25 is axially adjacent the apexes 57, and force is no longer acting, the retainer 37 maintains mechanical and electrical contact between the ring members 29, 31 and contact 25. The functions of the prior art connector block are thus satisfied in a block of contacts 23, without set screws. If preferred, however, for the security of employing two alternate systems of securing contacts and the lead, a set screw block or multiple blocks may be employed along with the split ring contacts 23, for one or more lead contacts 13.

The preferred embodiments of the invention, and the invention itself, are now described in such full, clear, concise and exact terms as to enable a person of ordinary skill in the art to make and use the invention. The invented connectors may be employed to connect leads and extensions to each other, extensions and IPGs to each other, and leads and IPGs directly. Thus, the invented connectors are not limited in use to connecting leads and extensions only. For this specification, the term "wire-like electrical conductor" refers to extensions and other wire-like electrically conductive members, as well as leads. Also, the invented connectors may be employed alone, or with other forms of connectors. Surgeons are known to prefer a positive tactile feel that a connection is completed. A detent mechanism or alternative satisfactory structure may be incorporated, for example to provide a click-fit recognizable by touch, sound or the like. A set screw is a possible alternative. Further, the term "body implantable apparatus" is used here to refer to implants such as described in the Background of The Invention, whether the whole of the apparatus is implantable, or otherwise. To particularly point and distinctly claim the subject matters regarded as invention, the following claims conclude this specification. To the extent variations from the preferred embodiments fall within the limits of the claims, they are considered to be part of the invention, and claimed.

What is claimed is:

1. In body implantable apparatus for implantation in a living body, for delivering electrical stimulation to the nervous system of the body, the apparatus including a wire-like electrical conductor, an improved electrical and mechanical connector for the conductor, comprising:

a multi-piece body forming a receptor for the conductor, at least one of the body pieces being electrically conductive; and an elastic member retaining together the body pieces of the multi-piece body, the elastic member biasing the body pieces into mechanical, restraining contact with the conductor, when the conductor is introduced into the receptor, and biasing the electrically conductive body piece into electrical contact with the conductor, when the conductor is introduced into the receptor, the elastic member further elastically yieldable under mechanical force to permit introduction of the conductor into the receptor.

2. In body implantable apparatus for implantation in a living body, for delivering electrical stimulation to the nervous system of the body, the apparatus including a wire-like electrical conductor, the improved electrical and mechanical connector for the conductor as in claim 1, the multi-piece body forming the receptor for the conductor including multiple duplicate pieces arranged circumferentially around the receptor, the elastic member circumferentially retaining together the body pieces.

3. In body implantable apparatus for implantation in a living body, for delivering electrical stimulation to the nervous system of the body, the apparatus including a wire-like electrical conductor, the improved electrical and mechanical connector for the conductor as in claim 2, the multi-piece body forming the receptor for the conductor consisting of two arcuate, duplicate pieces arranged circumferentially around the receptor.

4. In body implantable apparatus for implantation in a living body, for delivering electrical stimulation to the nervous system of the body, the apparatus including a wire-like electrical conductor, the improved electrical and mechanical connector for the conductor as in claim 3, the two arcuate, duplicate pieces of the multi-piece body being electrically conductive.

5. In body implantable apparatus for implantation in a living body, for delivering electrical stimulation to the nervous system of the body, the apparatus including a wire-like electrical conductor, the improved electrical and mechanical connector for the conductor as in claim 3, the receptor defining an axis for axial insertion of the lead, the two arcuate, duplicate pieces of the multi-piece body having conical insertion guiding surfaces.

6. In body implantable apparatus for implantation in a living body, for delivering electrical stimulation to the nervous system of the body, the apparatus including a wire-like electrical conductor, the improved electrical and mechanical connector for the conductor as in claim 5, the extent of the two arcuate, duplicate pieces along the axis defining a center of the pieces, the conical insertion guiding surfaces being sloped inwardly toward the center.

7. In body implantable apparatus for implantation in a living body, for delivering electrical stimulation to the nervous system of the body, the apparatus including a wire-like electrical conductor, the improved electrical and mechanical connector for the conductor as in claim 6, the two arcuate, duplicate pieces including duplicate conical insertion guiding surfaces sloped inwardly toward the center on both axial sides of the center.

8. In body implantable apparatus for implantation in a living body, for delivering electrical stimulation to the nervous system of the body, the apparatus including a wire-like electrical conductor, the improved electrical and mechanical connector for the conductor as in claim 6, the elastic member biasing the conical insertion guiding surfaces of the body pieces toward each other.

9. In body implantable apparatus for implantation in a living body, for delivering electrical stimulation to the nervous system of the body, the apparatus including a wire-like electrical conductor, the improved electrical and mechanical connector for the conductor as in claim 1, the elastic member including a superelastic material.

10. In body implantable apparatus for implantation in a living body, for delivering electrical stimulation to the nervous system of the body, the apparatus including a wire-like electrical conductor, the improved electrical and mechanical connector for the conductor as in claim 9, the superelastic material including nickel titanium alloy.

11. In body implantable apparatus for implantation in a living body, for delivering electrical stimulation to the nervous system of the body, the apparatus including a wire-like electrical conductor, the improved electrical and mechanical connector for the conductor as in claim 1, the elastic member including a superelastic material, and the elastic member having a C-shape.

12. In body implantable apparatus for implantation in a living human body, for delivering electrical stimulation to at least one nerve of the body, the apparatus including an implantable pulse generator (IPG), for generating the electrical stimulation, and an implantable wire-like electrical lead for delivering the stimulation from the IPG to the desired site of stimulation, the lead having a distal portion for placement at the site and a proximal portion, the proximal portion including multiple proximal electrical contacts, an improved connector block for electrical and mechanical connection of the proximal portion of the lead into the apparatus by connection to an extension, the improved connector block comprising:

a plurality of multi-piece bodies each forming a receptor opening for a proximal electrical contact, at least one of the body pieces of each body being electrically conductive adjacent the receptor opening; and a plurality of elastic members, each elastic member retaining together the body pieces of one of the multi-piece bodies, the elastic member biasing the body pieces into mechanical, fixating contact with a proximal electrical contact, when the contact is introduced into the receptor opening, and biasing the electrically conductive body piece into electrical contact with the proximal electrical contact, when the proximal electrical contact is introduced into the receptor opening, the elastic member further elastically yieldable under mechanical force to permit introduction of the proximal electrical contact into the receptor opening.

13. In body implantable apparatus as in claim 12, the improvement as in claim 12, each multi-piece body including multiple duplicate pieces arranged circumferentially around the receptor opening, the elastic member circumferentially retaining together the body pieces.

14. In body implantable apparatus as in claim 12, the improvement as in claim 12, each multi-piece body consisting of two arcuate, duplicate pieces arranged circumferentially around the receptor opening.

15. In body implantable apparatus as in claim 14, the improvement as in claim 14, the two arcuate, duplicate pieces of each multi-piece body being electrically conductive.

16. In body implantable apparatus as in claim 14, the improvement as in claim 14, each receptor opening defining an axis for axial insertion of the lead, the two arcuate, duplicate pieces of each multi-piece body having conical insertion guiding surfaces.

17. In body implantable apparatus as in claim 16, the improvement as in claim 16, the extent of the two arcuate, duplicate pieces along the axis defining a center of the pieces, the conical insertion guiding surfaces being sloped inwardly toward the center.

18. In body implantable apparatus as in claim 14, the improvement as in claim 14, the two arcuate, duplicate pieces including duplicate conical insertion guiding surfaces sloped inwardly toward the center on both axial sides of the center.

19. In body implantable apparatus as in claim 16, the improvement as in claim 16, the elastic member biasing the conical insertion guiding surfaces of the body pieces toward each other.

20. In body implantable apparatus as in claim 12, the improvement as in claim 12, the elastic member including a superelastic material.

21. In body implantable apparatus as in claim 20, the improvement as in claim 20, the superelastic material including nickel titanium alloy.

22. In body implantable apparatus as in claim 12, the improvement as in claim 12, the elastic member including a superelastic material, and the elastic member having a C-shape.

* * * * *